(12) United States Patent
Romari et al.

(10) Patent No.: US 9,556,468 B2
(45) Date of Patent: *Jan. 31, 2017

(54) PRODUCTION OF LUTEIN IN MIXOTROPHIC MODE BY SCENEDESMUS

(71) Applicant: FERMENTALG, Libourne (FR)

(72) Inventors: Khadidja Romari, Clermont-Ferrand (FR); Francois Godart, Genissac (FR); Pierre Calleja, Bordeaux (FR)

(73) Assignee: FERMENTALG, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/385,305

(22) PCT Filed: Mar. 15, 2013

(86) PCT No.: PCT/FR2013/050544
§ 371 (c)(1),
(2) Date: Sep. 15, 2014

(87) PCT Pub. No.: WO2013/136027
PCT Pub. Date: Sep. 19, 2013

(65) Prior Publication Data
US 2015/0037839 A1    Feb. 5, 2015

(30) Foreign Application Priority Data

Mar. 16, 2012 (FR) .................. 12 52381

(51) Int. Cl.
C12P 23/00    (2006.01)
C12R 1/89    (2006.01)
C12N 1/12    (2006.01)

(52) U.S. Cl.
CPC .............. *C12P 23/00* (2013.01); *C12N 1/12* (2013.01); *C12R 1/89* (2013.01)

(58) Field of Classification Search
CPC .............. A23L 1/19; C12P 23/00; C12R 1/89
See application file for complete search history.

(56) References Cited

U.S. PATENT DOCUMENTS

| | | | | |
|---|---|---|---|---|
| 3,316,674 A | * | 5/1967 | Minoru Shirota | A01G 33/00 435/257.3 |
| 3,444,647 A | * | 5/1969 | Takahashi | A01G 33/00 210/602 |
| 5,381,075 A | * | 1/1995 | Jordan | C12M 21/02 307/115 |
| 2006/0166343 A1 | * | 7/2006 | Hankamer | C12N 1/12 435/168 |
| 2007/0196893 A1 | * | 8/2007 | Weiss | A23L 1/2755 435/67 |
| 2009/0305942 A1 | * | 12/2009 | Day | C12P 7/6418 510/437 |

OTHER PUBLICATIONS

U.S. Appl. Nos. 13/822,805; 13/878,468; 14/124,367; 14/127,389; 14/124,829; 14/385,294; 14/385,502; 14/385,507.*

* cited by examiner

*Primary Examiner* — Ruth Davis
(74) *Attorney, Agent, or Firm* — Young & Thompson

(57) ABSTRACT

Novel strains of microalgae belonging to the *Scenedesmus* genus enable the production of lipids, in particular lutein, in mixotrophic mode, as well as a method for selecting and culturing the strains using a variable and/or discontinuous supply of light, in particular in the form of flashes.

7 Claims, No Drawings

PRODUCTION OF LUTEIN IN MIXOTROPHIC MODE BY SCENEDESMUS

The invention relates to a method of culture in mixotrophic mode, in the presence of a variable and/or discontinuous supply of light, in particular in the form of flashes, of a microalga of the genus *Scenedesmus*. The method makes it possible to obtain a high yield of biomass and an enrichment in lutein of the thus cultured microalgae. The invention also relates to a novel strain of microalga belonging to the genus *Scenedesmus*, particularly suitable for the production of carotenoids. This novel strain of *Scenedesmus* sp. is useful for producing lutein in mixotrophic mode.

Preamble

Microalgae are autotrophic photosynthetic microorganisms, i.e. they have the ability to grow autonomously by photosynthesis.

The microalgae develop equally well in the marine aquatic media as in fresh or brackish waters, as well as in various land habitats.

Most species of microalgae found in fresh water or in the oceans are generally autotrophic, i.e. they can only grow by photosynthesis.

For these species, the presence in their environment of carbon-containing substrates or organic matter is not favourable to them, and does not improve their growth. However, a certain number of species of microalgae, of very varied families and origins, are found not to be generally autotrophic. Thus, some of them, said to be heterotrophic, are capable of developing in the total absence of light, by fermentation, i.e. by using organic matter.

Other species of microalgae, for which photosynthesis remains essential for their development, are capable of benefiting both from photosynthesis and from organic matter present in their environment. These intermediate species, said to be mixotrophic, can be cultured in the presence of both light and organic matter.

This particularity of so-called "mixotrophic" algae seems to be related with their metabolism, which allows them to carry out photosynthesis and fermentation simultaneously. Both types of metabolism co-exist with a positive overall effect on the growth of the algae [Yang, C. et al. (2000); *Biochemical Engineering Journal*, 6:87-102].

Microalgae are currently the subject of numerous industrial projects since some species are capable of accumulating or secreting major quantities of carotenoids. Carotenoids, of which about 600 are known, are pigments tending to orange and yellow in colour, which are distributed in many living organisms. As they are liposoluble, they are in general easily assimilated by the organisms. They belong to the chemical family of the terpenoids, formed from the polymerization of isoprene units with an aliphatic or alicyclic structure. Included within the term "carotenoid" are the carotenes and the xanthophylls.

Carotenoids have several functions in microalgae. In fact, they are not only involved in a process of the absorption of light, but they also both contribute to the stabilization of the structure of the photosynthetic complexes and promote their function, as well as trapping active oxygen derivatives and dissipating excess energy. The intrinsic antioxidant activity of carotenoids constitutes the basis of their protective action against oxidative stress.

The antioxidant properties of these molecules are in fact very attractive for the food industry and the pharmaceutical industry. The addition of antioxidants to food products can inhibit or slow oxidation by free radicals, as well as interrupt the propagation of these chains of free radicals.

Carotenoids are used as pigments, but they also have an important role for human health as antioxidant agents. They also have the ability to stimulate the immune system.

Lutein (from the Latin luteus, yellow) ($C_{40}H_{56}O_2$) is a xanthophyll, found in egg yolk, yellow vegetables (maize, carrots) or those with green leaves (spinach, sorrel) and edible flowers such as marigold (Tagetes).

This molecule is currently used mainly as a colouring agent in the food industry. However, its increasing use as a food supplement is noted. Lutein, as well as zeaxanthin in much lesser larger quantities, are the only carotenoids which are absorbed into the blood after ingestion and accumulated in the human retina. Lutein is associated with a possible reduction in the risks linked to ocular and skin lesions caused by blue light. It is in particular associated with the prevention of age-related macular degeneration (ARMD).

Lutein is currently obtained from calendula petals after an extraction process that produces oleoresins at lutein concentrations varying between 5 and 50%, the majority being in the form of diester. The thus obtained lutein can be further purified by saponification, concentration and final recrystallization in order to produce its crystalline form. Lutein in crystalline form is nevertheless difficult to handle and is sold in suspension in maize or sunflower oil.

However, calendula has drawbacks as a source of lutein. The flowers must be collected periodically and the petals must be separated before the extraction. The lutein content in the petals is variable and can drop to 0.03%. As a result, the production of calendula petals is a process requiring intensive labour and large areas of production.

The production of lutein by the synthetic chemical route is much more expensive than the route by extraction from calendula. The other existing sources of lutein (shellfish, egg yolks) have a limited availability or have a quite low content (maize) to make these sources viable for the production of lutein on an industrial scale.

The production of the lutein by microalgae represents an advantageous alternative with respect to production via the chemical route as well as via the plant route. It requires a smaller input of manpower with respect to the plant route and is much more cost-effective with respect to the chemical route.

Therefore, novel sources of carotenoids, in particular lutein, have to be sought in order to meet, in the future, the increasing demand for these molecules.

At present, the classification of algae is still based widely on morphological criteria and on the character of the photosynthetic pigments that their cells contain. For this reason, it gives little information about the autotrophic, heterotrophic or mixotrophic character of the algal species, whereas the latter cover a very great diversity of species and forms [Dubinsky et al. (2010); *Hydrobiologia*, 639:153-171].

The taxonomic classification of eukaryotic algae contains 14 phyla. Large variations exist among the species of the different classes making up these phyla that produce fatty acids, as regards the carotenoids content of the microalgae. Moreover, the relative proportions of the different carotenoids, in particular lutein, in the lipid profiles, vary according to the species and the culture conditions.

To implement the production of fatty acids by microalgae on an industrial scale, several factors must be taken into account. For example, cultures may be carried out under autotrophic, mixotrophic or heterotrophic conditions depending on the strain, the temperature, the lighting conditions and the size of the fermenters. For example, cultures may both be carried out in 1L containers, in a laboratory, in photo-bioreactors, and in 100,000 L containers or in open ponds (several hectares). However, the costs of energy and other resources such as manpower and the ease of monitoring the culture must be taken into account for developing ideal culture conditions.

In any case, it is desirable that the microalgae are cultured under optimum conditions for increasing the yield of carotenoids to be produced. Thus, it is preferable to have a yield that is as high as possible (for example biomass above 30 g of dry matter per litre of culture, and more than 0.9% of carotenoids relative to the dry matter).

Among the different microalgae capable of producing lutein, only *Murielopsis* spp. and *Scenedesmus almeriensis* have been tested under culture conditions suitable for the production of lutein on a large scale.

*Scenedesmus* is a freshwater green microalga belonging to the order *Chloroccocales* and the family *Scenedesmaceae*. *Scenedesmus* appears in the form of coenobia containing 2, 4 or 8 cells which are linear or in alternating rows. The number of cells depends on the living conditions of the organism. The cells are ellipsoid or fusiform in shape, each having a plastid normally bearing a clearly visible pyrenoid. They have a width of 2.2 to 9.6 µm and a length of 6 to 15 µm. Multiplication takes place by autosporulation via the fractionation of the side walls of the cells: each cell reproducing a complete coenobium [Bourelly, P. (1966) Les algues d'eau douce. Initiation a la systématique. Vol I: Les Algues vertes].

In American patent U.S. Pat. No. 8,067,225, an autotrophic culture of *Scenedesmus almeriensis* in a 4000 L tubular reactor produced a biomass with a lutein content capable of reaching 0.5% of the dry biomass. The authors of this document found that a temperature of 30° C. and a pH at 8, without the addition of vitamins, were the most suitable conditions for the growth of *Scenedesmus almeriensis*.

In international patent application WO 2010/063256, cultured strains of *Scenedesmus* gave a lutein yield of 2 to 6 mg/g (0.6%) of dry matter. The cultures were carried out under autotrophic conditions, in a mineral medium comprising phosphates and nitrates in limited quantities, at a temperature comprised between 16 and 35° C. and at a pH comprised between 6 and 8.

In the article "*Effect of acetate on growth and ammonium uptake in the microalga Scenedesmus obliquus*", published in Physiologia Plantarum 1994, vol. 91, no.4, pp. 729-734, the strain *Scenedesmus obliquus* was tested under different culture conditions. Under mixotrophic conditions, the growth rate of the cells was greater than that obtained under autotrophic or heterotrophic culture conditions respectively (which gave similar results), in contrast to the observations with *S. falcatus*, which is capable of using acetate under illumination conditions, but is unable to grow under heterotrophic conditions [Fingergut, U., Groeneweg, J. & Soeder, C. J., Acetate utilization in *Scenedesmus falcatus*, an alga from high-rate ponds (1990), *Algol. Stud.* 60:57-64].

It would be desirable to be able to obtain greater yields of lutein for a more efficient and cost-effective industrial production.

Thus, it was after numerous experiments under unusual lighting conditions and with the addition of various substrates that the applicant succeeded in isolating microalgal strains of the genus *Scenedesmus* that can be cultured in mixotrophic mode, making possible, under the conditions of the present invention, a production of carotenoids, in particular lutein, at high yield.

One strain (FCC 174) representing novel strains of *Scenedesmus* sp. thus isolated and selected, was deposited at the CCAP (Culture Collection of Algae and Protozoa, Scottish Association for Marine Science, Dunstaffnage Marine Laboratory, Oban, Argyll PA37 1QA, Scotland, United Kingdom) according to the provisions of the Treaty of Budapest, on Mar. 8, 2012 under the accession number CCAP 276/75.

The method of culture and selection consisted more particularly of culturing the microalgae under mixotrophic conditions, in the presence of variable and/or discontinuous illumination, notably in the form of flashes, with a range of specific variations of light intensity and frequency.

The frequent alternation of illuminated phases and phases of darkness or of lower light intensity, generally perceived as stressful for microalgae, surprisingly, made it possible to obtain a high production of biomass, of carotenoids and more particularly of lutein, from the strains of *Scenedesmus* sp. The application of such strains according to the invention opens the perspective of industrial production of lutein, in fermenters benefiting from a reduced light supply, and should therefore make possible energy savings compared to autotrophic modes of culture.

The different aspects and advantages of the invention are detailed below.

DETAILED DESCRIPTION

The present invention therefore relates to a method of culture of microalgae of the genus *Scenedesmus*, in mixotrophic mode, under conditions of illumination that is discontinuous and/or variable over time. The illumination has variations in intensity, the amplitude of which is generally comprised between 5 $\mu mol \cdot m^{-2} \cdot s^{-1}$ and 1,000 $\mu mol \cdot m^{-2} \cdot s^{-1}$, preferably between 30 and 400 $\mu mol \cdot m^{-2} \cdot s^{-1}$. These variations may generally take place between 2 and 3,600 times per hour, preferably between 2 and 200 times per hour. These culture conditions make it possible to supply a defined quantity of light. This light supply may comprise phases of discontinuous and/or variable illumination, with variations in intensity that may have identical or different amplitudes. The illumination may in particular be in the form of flashes.

The advantage of this method is to increase the yield of biomass obtained from the culture. It also has the advantage of enriching with lutein the microalgae thus cultured. The other is to select strains of the genus *Scenedesmus*, with a mixotrophic character, and having a high yield of carotenoids, notably of lutein.

Culture of this microalga in mixotrophic mode is preferably carried out in the presence of 5 mM to 1 M, preferably from 50 mM to 800 mM, more preferentially from 70 mM to 600 mM, and even more preferentially from 100 mM to 500 mM of an organic carbon-containing substrate. The substrate is supplied continually during the culture, so as to allow the cells to accumulate a significant concentration of carotenoids. Additional substrate is added to the culture medium during the culture process so as to maintain a constant concentration. This organic carbon-containing substrate comprises preferentially, in pure form or as a mixture: glucose, derivatives of cellulose, lactate, starch, lactose, saccharose, acetate and/or glycerol.

The organic carbon-containing substrate contained in the culture medium may consist in complex molecules or in a mixture of substrates. The products resulting from the biotransformation of starch, for example starting from maize, wheat or potato, notably starch hydrolysates, which consist of small sized molecules, for example, form organic carbon-containing substrates which may be used for mixotrophic culture of the microalgae according to the invention.

This method is more particularly intended for the use of novel strains of microalgae of the genus *Scenedesmus* (Phylum: Chlorophyta, Order: Chlorococcales Family: Scenedesmaceae) [ITIS Catalogue of Life, 2010] selected for their mixotrophic character, notably for their capability to be cultured with a light supply greater than 10 µE, in a mineral medium, for example the BG11 medium [Rippka et al. (1979) Rippka, R., J. Deruelles, J. Waterbury, M. Herdman and R. Stanier, *Generic assignments, strain histories and properties of pure cultures of cyanobacteria*. J. Gen. Microbiol. 111: 1-61] to which an organic carbon-containing substrate is added. Preferably, the organic carbon-containing substrate comprises glucose, saccharose, at a concentration equivalent to or greater than 5 mM.

These novel strains of *Scenedesmus* sp. may be isolated and selected by the method of selection and culture according to the invention described below.

A representative strain of the *Scenedesmus* sp. strains according to the invention is the strain FCC 174 isolated by the applicant and deposited with the CCAP, on Mar. 8, 2012, under the accession number CCAP 276/75. These strains are capable of producing significant quantities of biomass as well as lutein, when they are cultured in mixotrophic mode with a variable or discontinuous light supply, according to the invention.

The invention relates to any strain *Scenedesmus* sp., capable of growing under mixotrophic culture conditions such as described in the present application, and capable of producing lutein. The invention also relates to any species of microalga of the genus *Scenedesmus*, capable of growing under mixotrophic culture conditions such as described in the present application, and capable of producing lutein.

The strains of *Scenedesmus* isolated according to the invention generally make it possible to produce, under mixotrophic conditions according to the invention, significant quantities of biomass of about 30-50 g/l, generally about 35-40 g/l. They also make it possible in this way to obtain lipids rich in lutein, said lutein being capable of representing more than 1% by weight with respect to the weight of dry matter. They also make it possible to obtain a yield of lutein of more than 10%, more than 25%, or also more than 50% of total hydrophobic matter contained in the microalgae. The hydrophobic matter of the microalga comprises lipids and carotenoids.

In the present invention, the lutein productivity obtained with the strain FCC 174, isolated by the applicant, from a culture under mixotrophic conditions in the presence of variable and/or discontinuous illumination, in particular in the form of flashes, may represent more than twice, generally more than 5 times the productivity of a culture with the same strain carried out in heterotrophic mode. By heterotrophic mode, it is meant culture conditions with an identical culture medium, but without a light supply.

The biomass obtained with the strain FCC 174, isolated by the applicant, from a culture under mixotrophic conditions in the presence of variable and/or discontinuous illumination, in particular in the form of flashes, is generally 50 to 100 times, generally 80 times greater than that of a culture with the same strain carried out in autotrophic mode.

The invention thus relates to a method for culturing microalgae of the genus *Scenedesmus*, in mixotrophic mode, in the presence of an illumination that is variable and/or discontinuous over time, for example, in the form of flashes, notably with a view to producing lutein.

The invention thus relates to a method for selecting microalgae of the genus *Scenedesmus*, with a mixotrophic character, and having a high yield of carotenoids, notably of lutein, in the presence of an illumination that is variable and/or discontinuous over time.

It appeared that variable and/or discontinuous illumination of the cultures, in particular when used in a culture in mixotrophic mode, had a favourable impact on the development of the algae and made it possible to increase the productivity of the latter, notably as far as their hydrophobic matter production is concerned. Without being bound to theory, the inventor believes that a discontinuous and/or variable light supply to the microalgae has the effect of causing a "stress" favourable to the growth and to the synthesis of carotenoids. This phenomenon may be partly explained by the fact that, in nature, microalgae tend to accumulate hydrophobic matter reserves to withstand the constraints of their environment.

By "discontinuous illumination", it is meant an illumination punctuated by periods of darkness. The periods of darkness may occupy more than a quarter of the time, preferably, half of the time or more, during which the algae are cultured.

According to a preferred aspect of the invention, the illumination is discontinuous and more preferentially in the form of flashes. A flash, within the meaning of the invention, is an illumination with light of short duration, i.e. of less than 30 minutes. The duration of the flash may be less than 15 minutes, preferably less than 5 minutes or even more preferentially less than 1 minute. According to certain embodiments of the invention, the duration of the flash may be less than a second. For example, the duration of the flash may be $1/10$ of a second, or $2/10$ of a second, or $3/10$ of a second, or $4/10$ of a second, or $5/10$ of a second, or $6/10$ of a second, or $7/10$ of a second, or $8/10$ of a second, or $9/10$ of a second. The illumination with light, or the flash, generally lasts longer than 15 seconds. The duration of the flash is generally comprised between 5 seconds and 10 minutes, preferably between 10 seconds and 2 minutes, more preferentially between 20 seconds and 1 minute.

In general, the number of flashes is comprised between about 2 and 3,600 per hour. It may be, for example, comprised between 100 and 3,600 flashes per hour. It may also be comprised between 120 and 3,000, or between 400 and 2,500, or between 600 and 2,000, or between 800 and 1,500 flashes per hour. It may also be comprised between 2 and 200, preferably between 10 and 150, more preferably between 15 and 100, and even more preferably between 20 and 50 per hour. The flashes may be emitted at regular or irregular time intervals. In the case of emission at regular intervals, the number of flashes per hour then corresponds to a frequency (F) having a time period (T), it being considered that F =1/T. This time period may be comprised between 1 second and 30 minutes, or between 1 second and 36 seconds, or between 1.2 second and 30 seconds, or between 1.44 second and 9 seconds, or between 1.8 second and 6 seconds, or between 2.4 seconds and 4.5 seconds. This frequency may also be comprised between 18 seconds and 30 minutes, preferentially between 24 seconds and 6 minutes, more preferentially between 36 seconds and 4 minutes, and even more preferentially between 72 seconds and 3 minutes. The number of flashes per hour is selected as a function of the intensity and duration of the flashes (see below). In general, the intensity of the light supplied in the form of flashes is comprised between 5 and 1000 $\mu mol \cdot m^{-2} \cdot s^{-1}$, preferably between 5 and 500 $\mu mol \cdot m^{-2} \cdot s^{-1}$, or 50 and 400 $\mu mol \cdot m^{-2} \cdot s^{-1}$, and more preferentially between 150 and 300 $\mu mol \cdot m^{-2} \cdot s^{-1}$. By definition, 1 $\mu mol \cdot m^{-2} \cdot s^{-1}$ correspond to 1 $\mu E \ m^{-2} \cdot s^{-1}$ (Einstein), a unit often used in the literature.

According to a particular embodiment of the invention, the intensity of the light is comprised between 50 and 200 $\mu mol \cdot m^{-2} \cdot s^{-1}$, the frequency of the flashes is comprised between 10 seconds and 60 minutes for a flash duration comprised between 1 second and 1 minute.

According to another embodiment of the invention, the illumination may be variable, which means that the illumination is not interrupted by phases of darkness, but instead the light intensity varies over time. This variation of the light intensity is regular and may be periodic or cyclic. According to the invention, light may also be supplied combining phases of continuous and discontinuous illumination.

According to the invention, regardless of the illumination conditions, the light intensity supplied to the algae in culture, expressed in micromoles of photons per second per square metre ($\mu mol \cdot m^{-2} \cdot s^{-1}$), varies at least once in any one hour. The amplitude of this variation of light intensity is generally comprised between 5 and 1,000, or between 50 and 800, or between 100 and 600 $\mu mol \cdot m^{-2} \cdot s^{-1}$. The intensity of the light may also vary between 5 and 400 $\mu mol \cdot m^{-2} \cdot s^{-1}$. Preferably, the amplitude of the variation of light intensity is between 70 and 300 $\mu mol \cdot m^{-2} \cdot s^{-1}$ and more preferentially between 100 and 200 $\mu mol \cdot m^{-2} \cdot s^{-1}$.

Said light intensity may attain successively, under conditions of variable illumination, for example, the values 50 $\mu mol \cdot m^{-2} \cdot s^{-1}$ and 100 $\mu mol \cdot m^{-2} \cdot s^{-1}$, or 5 and 400 $\mu mol \cdot m^{-2} \cdot s^{-1}$, or 50 and 800 $\mu mol \cdot m^{-2} \cdot s^{-1}$ several times every hour. Said light intensity may attain successively, preferably, the values 50 and 200 $\mu mol \cdot m^{-2} \cdot s^{-1}$. Alternatively, under conditions of discontinuous illumination, said light intensity may attain successively, several times per hour, for example, the values 0 and 50 $\mu mol \cdot m^{-2} \cdot s^{-1}$, the values 0 and 100 $\mu mol \cdot m^{-2} \cdot s^{-1}$ or still more preferentially the values 0 and 200 $\mu mol \cdot m^{-2} \cdot s^{-1}$. It may also attain successively, several times per hour, for example, the values 0 and 300 $\mu mol \cdot m^{-2} \cdot s^{-1}$, the values 0 and 600 $\mu mol \cdot m^{-2} \cdot s^{-1}$, the values 0 and 800 $\mu mol \cdot m^{-2} \cdot s^{-1}$ or also the values 0 and 1,000 $\mu mol \cdot m^{-2} \cdot s^{-1}$.

According to an embodiment of the invention, regardless of the illumination conditions, the intensity of the light supplied to the culture varies as a function of the cell density. The denser the culture becomes, the more intense the light may be. The cell density is the number of cells per ml and it is measured by the techniques known to one skilled in the art.

At the initial stage of the culture, when the cell density is between about $10^5$ and $5 \times 10^5$ cells per ml, the light intensity may be between 5 and 15 $\mu mol \cdot m^{-2} \cdot s^{-1}$, preferably between 5 and 10 $\mu mol \cdot m^{-2} \cdot s^{-1}$. When the culture reaches a density between $10^6$ and $10^7$ cells per ml, the light intensity may be increased to between 15 and 200 $\mu mol \cdot m^{-2} \cdot s^{-1}$, for example, preferably, between 20 and 50 $\mu mol \cdot m^{-2} \cdot s^{-1}$. When the culture, at the final stage, reaches a density between $10^7$ and $10^8$ cells per ml, the light intensity may be increased to between 50 and 400 $\mu mol \cdot m^{-2} \cdot s^{-1}$ for example, preferably between 50 and 150 $\mu mol \cdot m^{-2} \cdot s^{-1}$.

According to certain embodiments, for example, when the duration of the flashes is for example less than a minute, or less than a second, the intensity of the light may be higher than the values stated above. At the initial stage of the culture, when the cell density is between about $10^5$ and $5 \times 10^5$ cells per ml, the light intensity may be between 5 and 200 $\mu mol \cdot m^{-2} \cdot s^{-1}$, preferably between 5 and 100 $\mu mol \cdot m^{-2} \cdot s^{-1}$. When the culture reaches a density between $10^6$ and $10^7$ cells per ml, the light intensity may be increased to between 30 and 500 $\mu mol \cdot m^{-2} \cdot s^{-1}$, for example, preferably, between 50 and 400 $\mu mol \cdot m^{-2} \cdot s^{-1}$. When the culture, at the final stage, reaches a density between $10^7$ and $10^8$ cells per ml, the light intensity may be increased to between 100 and 1,000 $\mu mol \cdot m^{-2} \cdot s^{-1}$ for example, preferably, between 200 and 500 $\mu mol \cdot m^{-2} \cdot s^{-1}$.

According to an embodiment of the invention, the quantity of light supplied to the culture per hour remains between certain values. It is comprised between about 2,000 and 600,000, preferably between 2,000 and 300,000 $\mu mol \cdot m^{-2}$. It may be comprised between 4,000 and 200,000 $\mu mol \cdot m^{-2}$ per hour.

According to an embodiment of the invention, the culture is illuminated with 30 flashes per hour, each flash having a duration of 30 seconds and an intensity of 10 $\mu mol \cdot m^{-2} \cdot s^{-1}$. The latter gives a total supply of light per hour of 9,000 $\mu mol \cdot m^{-2}$. According to another embodiment of the invention, the culture is illuminated with 20 flashes per hour, each flash having a duration of 30 seconds and an intensity of 20 $\mu mol \cdot m^{-2, -1}$. The latter gives a total supply of light per hour of 12,000 $\mu mol \cdot m^{-2}$. According to another embodiment of the invention, the culture is illuminated with 45 flashes per hour, each flash having a duration of 15 seconds and an intensity of 5 $\mu mol \cdot m^{-2} \cdot s^{-1}$, which gives a total supply of light per hour of 3,375 $\mu mol \cdot m^{-2}$. According to another embodiment of the invention, the culture is illuminated with 120 flashes per hour, each flash having a duration of 10 seconds and an intensity of 200 $\mu mol \cdot m^{-2} \cdot s^{-1}$, which gives a total supply of light per hour of 240,000 $\mu mol \cdot m^{-2}$.

As described for the light intensity above, and according to an embodiment of the invention, the quantity of light supplied to the culture per hour may vary as a function of the cell density. At the initial stage of the culture, when the cell density is $10^5$ and $5 \times 10^5$ cells per ml, the total supply of light per hour is generally comprised between about 1,500 and 8,000, preferably 1,500 and 6,000 $\mu mol \cdot m^{-2}$, yet more preferably between 2,000 and 5,000 $\mu mol \cdot m^{-2}$. When the culture reaches a density between $10^6$ and $10^7$ cells per ml, the total supply of light per hour may be increased until between 6,000 and 67,000 $\mu mol \cdot m^{-2}$, preferably between 6,000 and 50,000, and yet more preferably between 12,000 and 45,000 $\mu mol \cdot m^{-2}$, for example. In the final stage of the culture, at a cell density between $10^7$ and $10^8$ cells per ml, the total supply of light per hour may be increased to between 45,000 and 300,000, for example preferably, between 45,000 and 200,000 $\mu mol \cdot m^{-2}$, and for example, yet more preferably, between 50,000 and 150,000 $\mu mol \cdot m^{-2}$.

According to an embodiment of the invention, at the initial stage of the culture (at a cell density between $10^5$ and $5 \times 10^5$ cells per ml), the culture is illuminated with 30 flashes per hour, each flash having a duration of 30 seconds and an intensity between 5 and 10 $\mu mol \cdot m^{-2} \cdot s^{-1}$, which gives a total supply of light per hour of 2,250 $\mu mol \cdot m^{-2}$ to 4,500 $\mu mol \cdot m^{-2}$. Then, at the intermediate stage (at a cell density between $10^6$ and $10^7$ cells per ml), the culture is illuminated with 30 flashes per hour, each flash having a duration of 30 seconds and an intensity between 15 and 50 $\mu mol \cdot m^{-2} \cdot s^{-1}$, which gives a total supply of light per hour of 13,500 to 45,000 $\mu mol \cdot m^{-2}$. Then, at the final stage of the culture (at a cell density between $10^7$ and $10^8$ cells per ml), the culture is illuminated with 30 flashes per hour, each flash having a duration of 30 seconds and an intensity between 50 and 150 $\mu mol \cdot m^{-2} \cdot s^{-1}$, which gives a total supply of light per hour of 45,000 to 135,000 $\mu mol \cdot m^{-2}$.

According to an embodiment of the invention, for example, when the duration of the flashes is for example less than a minute, or less than a second, at the initial stage of the culture (at a cell density between $10^5$ and $5 \times 10^5$ cells per ml), the culture is illuminated with 30 flashes per hour, each flash having a duration of 10 seconds and an intensity between 50 and 100 µmol·m$^{-2}$·s$^{-1}$, which gives a total supply of light per hour of 15,000 µmol·m$^{-2}$ to 30,000 mol·m$^{-2}$. Then at the intermediate stage (at a cell density between 10$^6$ and 10$^7$ cells per ml), the culture is illuminated with 50 flashes per hour, each flash having a duration of 10 seconds and an intensity between 200 and 300 µmol·m$^{-2}$·s$^{-1}$, which gives a total supply of light per hour of 100,000 to 150,000 µmol·m$^{-2}$. Then, at the final stage of the culture (at a cell density between 10$^7$ and 10$^8$ cells per ml), the culture is illuminated with 120 flashes per hour, each flash having a duration of 10 seconds and an intensity between 350 and 450 µmol·m$^{-2}$·s$^{-1}$, which gives a total supply of light per hour of 420,000 to 540,000 µmol·m$^{-2}$.

The light supply to the cultures may be obtained by lamps distributed around the external wall of the fermenters. A clock triggers these lamps for defined illumination times. The fermenters are preferentially located in an enclosure, shielded from daylight, whose ambient temperature may be controlled.

As the applicant could ascertain, the fact that the thus selected strains have good growth capabilities in mixotrophic mode, in the presence of discontinuous and/or variable light, predisposes said strains to a higher production of carotenoids, in particular of lutein.

The method of culture according to the invention thus allows selection of strains of the genus *Scenedesmus*, with mixotrophic character, similar to that isolated by the applicant and deposited at the CCAP under the accession number CCAP 276/75, and having a high yield of lutein. This method of culture is characterized in that it comprises the following steps:

a) culture, in mixotrophic mode, of one or more strains of the genus *Scenedesmus*, under conditions of illumination that is discontinuous and/or variable over time, the illumination having variations in intensity, the amplitude of which is comprised between 5 µmol·m$^{-2}$·s$^{-1}$ and 1,000, preferably between 5 and 400 µmol·m$^{-2}$·s$^{-1}$, these variations taking place between 2 and 3,600, preferably 5-400 times per hour, b) a step of maintaining said culture over several generations, in the presence of an organic carbon-containing substrate in the culture medium, and optionally c) a step of recovery of the thus cultured microalgae.

By "step of recovery", it is meant more particularly the isolation of the strain or strains for which the number of cells increased the most during said generations.

For carrying out selection of the strains, different strains of the genus *Scenedesmus* may be cultured, in parallel, on microplates in one and the same enclosure, with precise monitoring of the conditions and evolution of the different cultures. It is, thus, easy to determine the response of the different strains to discontinuous and/or variable illumination and, if applicable, to the addition of one or more organic carbon-containing substrates to the culture medium. The strains that respond favourably to the discontinuous and/or variable illumination and to the organic carbon-containing substrates, generally provide a better yield for the production of lipids in terms of quality (lutein is more abundant in the lipid profile) and in terms of quantity (the lipids contain a higher proportion of lutein).

The microalgae may be selected in a fermenter from a heterogeneous population, and from one aims to select the variants favoured by the manner of selection according to the invention, combining discontinuous and/or variable light, having a specific range of light intensity and a specific frequency, with mixotrophic culture conditions. In this case, culture is carried out by maintaining the microalgae in culture over many generations, and then an isolation of the components that have become predominant in the culture medium, is performed at the end of culture.

The method of culture according to the invention also makes it possible to produce lutein.

In this case, the method according to the invention further comprises the following steps:

d) a step of recovery of the hydrophobic matter, and optionally e) the extraction of the lutein from the hydrophobic matter recovered.

The method of culture according to the invention may also be applied to any species of the genus *Scenedesmus*, capable of growing under the mixotrophic conditions according to the invention, and capable of producing lutein.

The method of culture according to the invention makes it possible to optimize the production of the biomass obtained from the culture. It also makes it possible to enrich the thus cultured microalgae in carotenoids, notably in lutein.

Therefore, the invention is also directed to optimizing the production of biomass, as well as the production of carotenoids, notably of lutein, through the culture of microalgae of the genus *Scenedesmus* with mixotrophic character, preferably cultured or selected according to the methods mentioned above, then the recovery of the thus cultured microalgae in order to extract the hydrophobic content therefrom, in particular lutein. The strains of the species *Scenedesmus* sp. are especially concerned.

The methods for extracting and analysing the carotenoids, including lutein, are known to one skilled in the art and are, for example, described by S .W . Wright et al., [Wright, S. W. et al. (1991): Improved HPLC method for the analysis of chlorophylls and carotenoids from marine phytoplankton. *Marine ecology progress series*: Vol. 77: 183-196)].

The invention also relates to the microalgae of the genus *Scenedesmus*, capable of being obtained according to the method of the invention as previously described. These microalgae are enriched in lutein. The hydrophobic matter of such microalgae generally comprises more than 10%, more than 25%, or also more than 50% of the lutein with respect to the total percentage of the hydrophobic matter.

EXAMPLE 1

The cultures of *Scenedesmus* sp. FCC 174 are carried out in 2L usable capacity fermenters (bioreactors) with dedicated automatic controllers and computerized supervision. The pH of the system is adjusted by adding base (a 1N sodium hydroxide solution) and/or acid (a 1N sulphuric acid solution). The culture temperature is set to 25° C. Stirring is achieved with 2 stirring rotors mounted on the shaft according to the Rushton configuration: three-blade impellers with downward pumping. The stirring speed and the air flow rate are regulated to a minimum=200 rpm and to a maximum=600 rpm and Qmin=0.5 vvm/Qmax=2 vvm respectively. The bioreactor is equipped with an external lighting system surrounding the transparent tank. The intensity as well as the light cycles are controlled by a dedicated automatic device and are under computerized supervision.

The reactors are inoculated with a preculture prepared on a stirring table (140 rpm) in a controlled-temperature enclosure (25° C.) and illuminated between 80 and 100 µE. Pre-cultures and cultures in bioreactors are carried out in the BG11 medium enriched in nitrogen [Rippka et al. 1979]. The organic carbon-containing substrate used for the culture in mixotrophic mode in a bioreactor is glucose at concentrations between 100 mM and 150 mM.

Monitoring of the Cultures:

The total biomass concentration is monitored by measuring the dry mass (filtration on a Whatman GFB filter, then oven drying in vacuo, at 65° C. and −0.8 bar, for a minimum of 24 h before weighing).

Regarding the quantification of the total lipids, $10^8$ cells/mL were extracted. Methods for extracting lipids are known to one skilled in the art and are, for example, described by [Bligh, E. G. and Dyer, W. J. (1959); A rapid method of total lipid extraction and purification, *Can J. Biochem. Physiol* 37:911-917].

Illumination:

The culture is illuminated with 120 flashes per hour, each flash having a duration of 10 seconds and an intensity of 200 $\mu mol \cdot m^{-2} \cdot 1$.

The light supply to the cultures in the bioreactor was obtained by LED (light-emitting diode) lamps distributed around the external wall of the fermenter. A clock triggers these LEDs for illumination times or pulses.

Results (n=3):

|  | Dry mass (g/L) | Total lipids (% of dry mass) | Lutein (mg/g of MS) |
| --- | --- | --- | --- |
| Mixotrophy with flash | 38 +/− 1.1 | 11.3 +/− 1.2 | 9.2 +/− 0.1 |
| Heterotrophy | 36.1 +/− 1.5 | 10.5 +/− 0.9 | 1.5 +/− 0.1 |

The invention claimed is:

1. A method for increasing the production of lutein in a culture of microalgae of the genus *Scenedesmus*, comprising the following steps:
    a) culturing, in mixotrophic mode, of one or more strains of microalga of the genus *Scenedesmus*, over several generations in a culture medium comprising a carbon-containing substrate selected from the group consisting of starch, lactate, lactose, saccharose, acetate, glycerol, glucose, cellulose derivatives and mixtures thereof, under conditions of illumination that is discontinuous, with alternation of illuminated phases and phases of darkness,
    wherein the illumination is in the form of flashes of light, said flashes having a duration of between 5 seconds to 10 minutes, with an intensity between 50 $\mu mol \cdot m^{-2} \cdot s^{-1}$ and 1000 $\mu mol \cdot m^{-2} \cdot s^{-1}$, said flashes occurring between 2 and 200 times per hour,
    and wherein the phases of darkness occupy at least half of the time during which the algae are cultured; and
    b) harvesting the cultured *Scenedesmus* microalgae cells, the cells being charged with lutein; and optionally
    c) recovering the lutein.

2. The method according to claim 1, wherein the organic carbon-containing substrate in the culture medium is at a concentration from 5 mM to 1 M, or from 50 mM to 800 mM, or from 70 mM to 600 mM, or from 100 mM to 500 mM.

3. The method according to claim 2, wherein said organic carbon-containing substrate is glucose, and the glucose is present at a concentration of at least 5 mM.

4. The method according to claim 1, wherein said flashes of light have a duration of between 10 seconds and 2 minutes, or between 20 seconds and 1 minute.

5. The method according to claim 1, wherein the number of flashes of light is between 10 and 150, or between 15 and 100, or between 20 and 50 times per hour.

6. The method according to claim 1, wherein the total amount of light in the illumination, per hour in micromoles of photons, is between 2,000 to 600,000, or between 2,000 to 200,000 $\mu mol \cdot m^{-2}$.

7. The method according to claim 1, wherein said microalga of the genus *Scenedesmus* corresponds to the strain FCC 174, deposited on Mar. 8, 2012, with the CCAP (Culture Collection of Algae and Protozoa), under the accession number CCAP 276/75.

* * * * *